(12) United States Patent
Kadokura et al.

(10) Patent No.: US 10,617,483 B2
(45) Date of Patent: Apr. 14, 2020

(54) SURGICAL INSTRUMENT STEERING INPUTS

(71) Applicant: Intuitive Surgical Operations, Inc., Sunnyvale, CA (US)

(72) Inventors: Grant M. Kadokura, Redwood City, CA (US); William A. McDonald, II, Sonora, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 238 days.

(21) Appl. No.: 15/782,322

(22) Filed: Oct. 12, 2017

(65) Prior Publication Data

US 2018/0104011 A1    Apr. 19, 2018

Related U.S. Application Data

(60) Provisional application No. 62/408,365, filed on Oct. 14, 2016.

(51) Int. Cl.
| | |
|---|---|
| *A61B 34/00* | (2016.01) |
| *A61B 17/00* | (2006.01) |
| *A61B 34/30* | (2016.01) |
| *A61B 17/29* | (2006.01) |
| *A61B 17/16* | (2006.01) |
| *A61B 90/00* | (2016.01) |

(52) U.S. Cl.
CPC ........ *A61B 34/71* (2016.02); *A61B 17/00234* (2013.01); *A61B 34/30* (2016.02); *A61B 17/1631* (2013.01); *A61B 2017/00367* (2013.01); *A61B 2017/00477* (2013.01); *A61B 2017/2901* (2013.01); *A61B 2034/301* (2016.02); *A61B 2034/302* (2016.02); *A61B 2034/715* (2016.02); *A61B 2090/031* (2016.02)

(58) Field of Classification Search
CPC ........ A61B 2034/302; A61B 2034/715; A61B 2090/031; A61B 17/1631; A61B 2017/2901
See application file for complete search history.

(56) References Cited

U.S. PATENT DOCUMENTS

| | | | | |
|---|---|---|---|---|
| 2011/0213383 | A1* | 9/2011 | Lee | A61B 34/71 606/130 |
| 2013/0331857 | A9* | 12/2013 | Prisco | A61B 34/30 606/130 |
| 2015/0051034 | A1 | 2/2015 | Cooper et al. | |
| 2018/0104011 | A1* | 4/2018 | Kadokura | A61B 34/71 |
| 2018/0104012 | A1* | 4/2018 | Wixey | A61B 34/71 |

* cited by examiner

*Primary Examiner* — Vicky A Johnson
(74) *Attorney, Agent, or Firm* — Fish & Richardson P.C.

(57) ABSTRACT

A surgical instrument includes: an adjustable end effector; an elongated instrument shaft defining an internal bore; and a drive assembly including a housing coupled to an end of the instrument shaft and an input device configured to facilitate controlled adjustment of the end effector via a drive cable extending along the bore of the instrument shaft. The input device includes: a drive shaft attached to a first portion of the drive cable, the drive shaft including an upstanding stem portion having a radially tapered outer surface; and a capstan attached to a second portion of the drive cable, the capstan defining an internal bore sized to receive the stem portion of the drive shaft, at least a lower portion of the internal bore having a radially tapered inner surface. The capstan and drive shaft are configured to transition from a disengaged state to an engaged state.

17 Claims, 11 Drawing Sheets

SURGICAL INSTRUMENT STEERING INPUTS

CROSS REFERENCE TO RELATED APPLICATIONS

This application claims the benefit of U.S. Provisional Application No. 62/408,365, filed Oct. 14, 2016. The disclosure of the prior application is considered part of and is incorporated by reference in the disclosure of this application.

TECHNICAL FIELD

This specification generally relates to surgical instruments for use with teleoperated robotic systems. In particular, the present disclosure describes steering input devices incorporated in such surgical instruments.

BACKGROUND

Minimally invasive medical techniques (e.g., laparoscopy) have been used to reduce the amount of extraneous tissue which may be damaged during diagnostic or surgical procedures, thereby reducing patient recovery time, discomfort, and deleterious side effects. Such techniques were traditionally performed manually via a surgeon manipulating various surgical instruments within the patient's body, but can now by implemented using teleoperated robotic systems that provide telepresence. Performing minimally invasive surgery with teleoperated robotic systems facilitates increased precision and range of motion in manipulating surgical instruments when compared to manual techniques, but also introduces new challenges. One such challenge is the need to manufacture, assemble, and tune (or "pre-tension") surgical instruments. Pre-tensioning tension actuation elements, such as cables or cable-hypotube combinations, enables the instruments' end effectors at the surgical site to respond rapidly and accurately to remote actuating signals. Conventional mechanically actuated surgical instruments include steering input devices that can be prohibitively expensive to produce in certain applications because they include multiple intricate components that must be machined to precise tolerances. Further, their means of assembly tends to make multi-step pre-tensioning procedures cumbersome and difficult to automate.

SUMMARY

One aspect of the present disclosure features a surgical instrument including: an adjustable end effector; an elongated instrument shaft defining an internal bore and extending from a first end coupled to the end effector to a second end; and a drive assembly including a housing coupled to the second end of the instrument shaft and an input device configured to facilitate controlled adjustment of the end effector via a drive cable extending along the bore of the instrument shaft. The input device includes: a drive shaft attached to a first portion of the drive cable, the drive shaft including an upstanding stem portion having a radially tapered outer surface; and a capstan attached to a second portion of the drive cable, the capstan defining an internal bore sized to receive the stem portion of the drive shaft, at least a lower portion of the internal bore having a radially tapered inner surface. The capstan and drive shaft are configured to transition from a disengaged state, where the capstan is freely rotatable about a longitudinal axis of the drive shaft, to an engaged state, where surface friction between the radially tapered surfaces of the drive shaft and capstan inhibits relative rotation as the end effector is adjusted during a surgical procedure.

In some examples, the outer surface of the stem portion of the drive shaft and the inner surface of the lower portion of the internal bore of the capstan are rounded and smooth, forming a keyless and unthreaded frictional coupling in the engaged state.

In some examples, the radial taper of the surfaces defines a self-locking taper angle, such that the capstan and drive shaft remain in the engaged state absent an external force. In some examples, the self-locking taper angle is less than about 1.5 degrees.

In some examples, a head portion of the capstan includes a structural coupling feature configured to facilitate engagement with an external device for rotating the capstan in the disengaged state. In some examples, the structural coupling feature includes a pair of opposing rectangular notches formed on an outer surface of the capstan.

In some examples, an upper portion of the internal bore of the capstan is coaxially aligned with a blind bore of the stem portion of the drive shaft. In some examples, the upper portion of the internal bore includes a pattern of threads for interfacing with a threaded lead screw, and the blind bore of the stem portion includes and undercut surface for supporting the lead screw. In some examples, the blind bore of the stem portion includes a pattern of threads for interfacing with a threaded mechanical fastener projecting through the coaxially aligned bores of the drive shaft and capstan, the mechanical fastener applying a constant axial force against the drive shaft and capstan to augment the surface friction.

Another aspect of the present disclosure features a method of tensioning a cable of a drive assembly for a surgical instrument having an adjustable end effector, including the steps of: aligning a capstan with a drive shaft of the drive assembly in a disengaged state; coupling respective portions of the cable to the drive shaft and to the capstan; then independently rotating the drive shaft and the capstan about a common longitudinal axis to tension the cable; and after tensioning the cable, securing the capstan to the drive shaft in an engaged state. The drive shaft includes an upstanding stem portion having a radially tapered outer surface, and the capstan includes an internal bore having a radially tapered inner surface, with at least a lower portion of the bore receiving the stem portion. Securing the capstan includes forcing the radially tapered inner surface of the internal bore of the capstan against the radially tapered outer surface of the stem portion of the drive shaft, such that surface friction between the radially tapered surfaces inhibits relative rotation between the drive shaft and capstan as the end effector is adjusted during a surgical procedure.

In some examples, rotating the capstan includes driving the capstan rotationally about the stem portion of the drive shaft.

In some examples, independently rotating the drive shaft and the capstan includes simultaneously rotating the drive shaft and capstan in opposite angular directions.

In some examples, aligning the capstan with the drive shaft includes placing the capstan over the drive shaft absent external force.

In some examples, securing the capstan to the drive shaft in an engaged state includes applying a vertical force against the capstan to drive the capstan down against the stem portion of the drive shaft.

In some examples, the radial taper of the surfaces defines a self-locking taper angle, such that the capstan and drive shaft remain in the engaged state absent an external force. In some examples, the self-locking taper angle is less than about 1.5 degrees.

In some examples, the method further includes the steps of: releasing the capstan from the drive shaft to transition from the engaged state to the disengaged state; further tensioning the cable to a predetermined set point by independently rotating the drive shaft and the capstan; and after further tensioning the cable, re-securing the capstan to the drive shaft to transition from the disengaged state to the engaged state. In some examples, releasing the capstan from the drive shaft includes the steps of: inserting a lead screw into the internal bore of the capstan, and urging the capstan to move along a threaded shaft of the lead screw as the lead screw bears against a surface of the drive shaft.

In some examples, securing the capstan to the drive shaft further includes inserting a set screw into an upper portion of the internal bore of the capstan and a blind bore of the stem portion of the drive shaft, the blind bore being coaxially aligned with the internal bore.

Yet another aspect of the present disclosure features a surgical instrument including: an adjustable end effector; an elongated instrument shaft defining an internal bore and extending from a first end coupled to the end effector to a second end; and a drive assembly including a housing coupled to the second end of the instrument shaft and an input device configured to facilitate controlled adjustment of the end effector via a drive cable extending along the bore of the instrument shaft. The input device includes: a drive shaft attached to a first portion of the drive cable, the drive shaft including a central blind bore; a capstan attached to a second portion of the drive cable, the capstan defining a central through-bore co-axially alignable with the blind bore of the drive shaft, and a set screw including a radially enlarged head centered atop an elongated shaft, the shaft including an upper portion sized to penetrate the through-bore of the capstan and a lower portion sized to penetrate the blind bore of the drive shaft. The capstan and drive shaft are configured to transition from a disengaged state, where the capstan is freely rotatable about the upper portion of the shaft of the set screw, to an engaged state, where a compressive clamping force between the set screw and drive shaft locks the capstan in place to inhibit relative rotation as the end effector is adjusted during a surgical procedure.

In some examples, the upper portion of the shaft of the set screw has a larger diameter than the lower portion of the shaft.

In some examples, an inner surface of the through-bore of the capstan and an outer surface of the upper portion of the shaft of the set screw are rounded and smooth, forming a keyless and unthreaded engagement.

In some examples, the head of the set screw includes a blind bore having a keyed profile for engaging a wrench device.

In some examples, the lower portion of the shaft of the set screw includes a set of exterior threads configured to mate with a complementary set of interior threads of the blind bore of the drive shaft.

In some examples, the surgical instrument further includes a first toothed washer residing axially between the head of the set screw and the capstan, and a second toothed washer residing axially between the capstan and the drive shaft. In some examples, the hardness of the material composition of each of the toothed washers is greater than the hardness of the material composition of the capstan.

In some examples, the drive shaft includes an upstanding stem portion having a radially tapered outer surface. In some examples, the through-bore of the capstan includes a radially tapered inner surface sized to receive the stem portion of the drive shaft.

Still another aspect of the present disclosure features a method of tensioning a cable of a drive assembly for a surgical instrument having an adjustable end effector including the steps of: aligning a capstan with a drive shaft of the drive assembly; coupling the capstan to the drive shaft in a disengaged state; coupling respective portions of the cable to the drive shaft and to the capstan; then rotating the capstan relative to the drive shaft to tension the cable; and after tensioning the cable, securing the capstan to the drive shaft in an engaged state. The drive shaft includes a central blind bore, and the capstan defines a central through-bore, and the aligning of the capstan and drive shaft places the blind bore into a co-axial alignment with the through-bore. Coupling the capstan to the drive shaft includes inserting a shaft of a set screw into the co-axially aligned through-bore of the capstan and blind bore of the drive shaft. Securing the capstan to the drive shaft includes clamping the capstan between a head of the set screw and the drive shaft with sufficient compressive force to lock the capstan in place, which inhibits relative rotation between the drive shaft and capstan as the end effector is adjusted during a surgical procedure.

In some examples, coupling the capstan to the drive shaft further includes engaging a set of exterior screw threads on the shaft of the set screw with a set of interior screw threads of the blind bore of the drive shaft. In some examples, securing the capstan to the drive shaft includes rotating the set screw to advance the shaft of the set screw through the blind bore of the drive shaft along the set of interior screw threads. In some examples, rotating the set screw includes driving the set screw with a wrench device engaged with a keyed blind bore on a radially enlarged head of the set screw.

In some examples, inserting the shaft of the set screw includes lowering the set screw downward relative to the capstan and drive shaft.

In some examples, aligning the capstan with the drive shaft includes placing the capstan over the drive shaft absent external force.

In some examples, rotating the capstan includes driving the capstan rotationally about an upper portion of the shaft of the set screw. In some examples, driving the capstan includes the steps of: placing a tensioning tool over a portion of the set screw and the capstan; keying a bore of the tensioning tool to a head portion of the capstan; engaging a tensioning wand to the tensioning tool; and exerting a force on the tensioning wand in a direction tangential to the head portion of the capstan.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

One or more of the illustrated elements may be exaggerated to better show the features, process steps, and results. Like reference numbers and designations in the various drawings may indicate like elements.

DETAILED DESCRIPTION

Various embodiments of the present disclosure relate to surgical instruments for use with teleoperated robotic systems. More specifically, embodiments include drive assemblies for surgical instruments featuring steering input devices that are more efficiently manufactured, assembled, and/or tuned than in prior systems. For example, the input devices featured in certain embodiments include multiple components that can be manufactured by molding instead of machining. Further, certain embodiments provide drive assemblies that include a quick engage-release coupling that can be assembled (and disassembled) without special tools or fasteners. This simplifies the tuning (e.g., drive cable pre-tensioning) process, enabling full or partial automation. Still further embodiments provide input devices that are capable of withstanding high torque loads and specifically configured for use in applications requiring a compact footprint.

Minimally invasive surgery can be performed by inserting surgical instruments through orifices in a patient's body (e.g., natural orifices or body wall incisions) and controlling the surgical instruments via an interface on the outside of the body. In various embodiments of the present disclosure, the surgical instruments are teleoperated by surgeons. Thus, the surgeons do not move the instruments by direct physical contact, but instead control instrument motion from some distance away by moving master input devices ("masters"). The operating surgeon is typically provided with a view of the actual surgical site via a visual display, so that the surgeon may remotely perform surgical motions with the masters while viewing the surgical site. A controller of the surgical system causes the surgical instrument to be moved in accordance with movement of a master.

Figure 1:
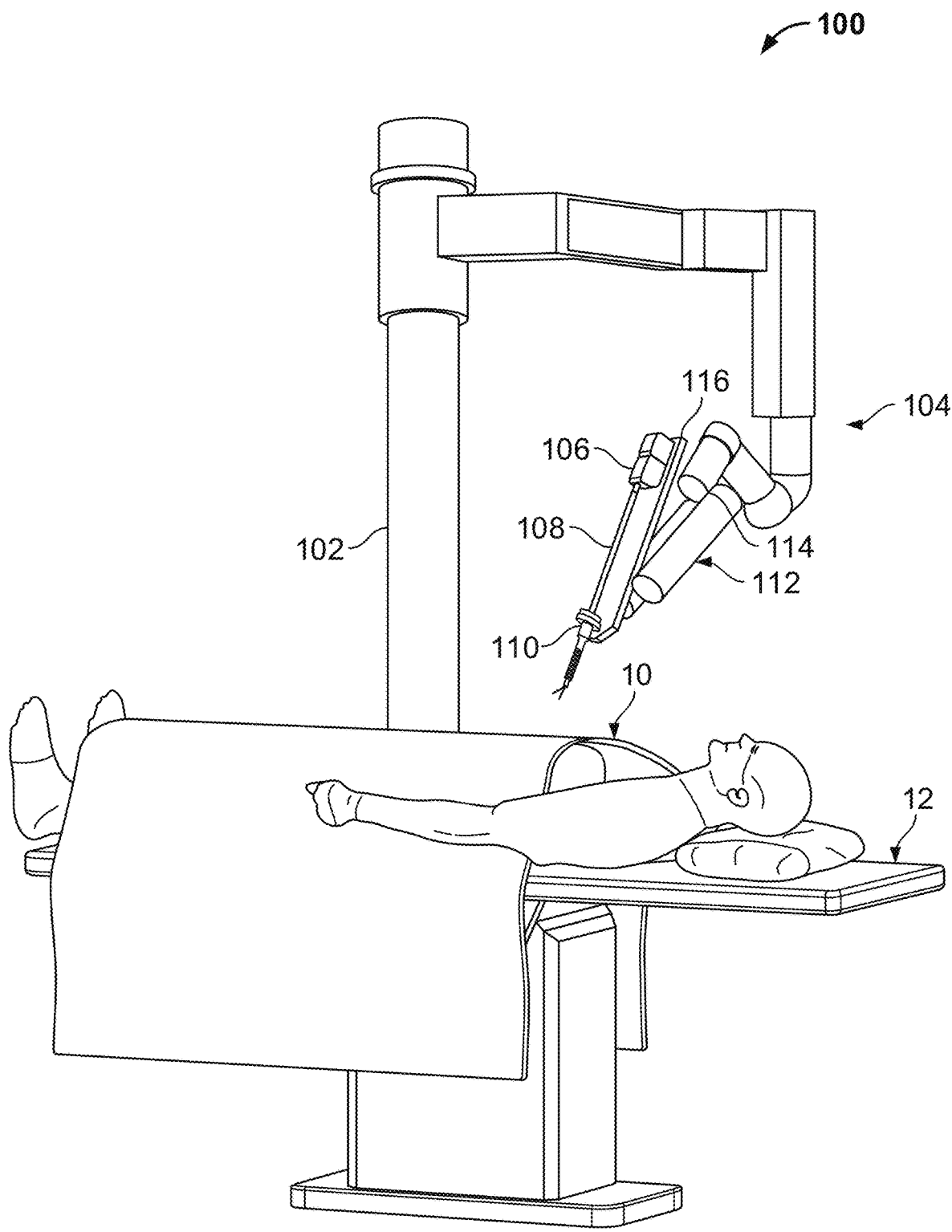
FIG. 1 is a perspective view of a portion of a teleoperated surgical system including a surgical instrument in accordance with one or more embodiments of the present disclosure.

FIG. 1 depicts a patient-side portion 100 of a teleoperated surgical system in accordance with one or more embodiments of the present invention. Patient-side portion 100 is a teleoperated robotic system for performing minimally invasive surgery on a patient's body 10 positioned on an operating table 12. Patient-side portion 100 includes a column 102, a support assembly 104, and an instrument carriage 106. In this example, column 102 anchors patient-side portion 100 on a floor surface (not shown) proximate operating table 12. However, in other embodiments the patient-side portion may be mounted to a wall, to the ceiling, to the operating table supporting the patient's body, or to other operating room equipment. Support assembly 104 branches radially outward from the column 102, and instrument carriage 106 resides at a distal end of the support assembly. Instrument carriage 106 supports a detachable surgical instrument 108, and the carriage includes various actuators and control connections for controlling functionality of the instrument during a surgical procedure within the patient's body 10. In particular, the teleoperated actuators housed in instrument carriage 106 provide a number of controller motions that surgical instrument 108 translates into a corresponding variety of movements of the instrument's end effector. In some examples, the surgical instrument includes a drive assembly housing an input device configured to facilitate controlled adjustment of the end effector in response to actuation signals from the instrument carriage. The particulars of the instrument's drive assembly and its individual components are provided below with reference to FIGS. 2A-4B.

Returning to FIG. 1, an entry guide 110 (e.g., a cannula) serves as a surgical port to an orifice of the patient's body 10 that receives surgical instrument 108 to guide the instrument into the patient. Entry guide 110 may perform various other functions, such as allowing fluids and other materials to pass into or out of the body and reducing trauma at the surgical site by isolating at least some motion of the surgical instrument (e.g., translating movement along an insertion axis, and/or axial (lengthwise) rotation of the instrument shaft around the insertion axis) from the body wall.

Support assembly 104 further includes an instrument manipulator 112 that controls positioning of surgical instrument 108 relative to the patient's body 10. In various implementations, instrument manipulator 112 may be provided in a variety of forms that allow surgical instrument 108 to move with one or more mechanical degrees of freedom (e.g., all six Cartesian degrees of freedom, five or fewer Cartesian degrees of freedom, etc.). Typically, mechanical or control constraints restrict instrument manipulator 112 to move surgical instrument 108 around a particular center of motion that stays stationary with reference to the patient's body 10. This center of motion is typically located proximate where surgical instrument 108 enters the patient's body 10 (e.g., at some point along entry guide 110, such as at the midpoint of the body wall). In this example, instrument manipulator 112 includes a joint 114 and an elongated spar 116 supporting instrument carriage 106 and entry guide 110. In this example, instrument carriage 106 is mounted to ride along the length of spar 116 while entry guide 110 is held fixed, so as to translate surgical instrument 108 through the entry guide along an insertion axis relative to the patient's body 10. Adjusting joint 114 locates surgical instrument 108 at a desired angular orientation about the center of motion, while movement of carriage 106 along spar 116 locates the surgical instrument at a desired insertion point through the center of motion. Thus, the teleoperated actuators of instrument manipulator 112 move surgical instrument 108 as a whole, as compared to the teleoperated actuators housed in instrument carriage 106, which move only the instrument's end effector or other individual instrument components. Manipulator 112 is illustrative of both manipulators that are configured to constrain the remote center of motion by fixed intersecting manipulator joint axes (hardware-constrained remote center of motion) and manipulators controlled by software to keep a defined remote center of motion fixed in space (software-constrained remote center of motion).

The term "surgical instrument" is used herein to describe a medical device for insertion into a patient's body and use in performing surgical or diagnostic procedures. A surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments appropriate for use in one or more embodiments of the present disclosure may control their end effectors (surgical tools) with one or more rods and/or flexible cables. In some examples, rods, which may be in the form of tubes, may be combined with cables to provide a pull, push, or combined "push/pull" or "pull/pull" control of the end effector, with the cables providing flexible sections as required. A typical elongate shaft for a surgical instrument is small, for example five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The rods and cables must fit within the elongate shaft and be able to control the end effector through the wrist joint. The cables may be manufactured from a variety of metal (e.g., tungsten or stainless steel) or polymer (e.g., high molecular weight polyethylene) materials. Polymer cables may be preferred in some embodiments to enable a discrete, multi-step pre-tensioning process. Polymer cables may be more suitable for such processes because they are not as stiff as metal cables and tend to release unintentional over-tensioning.

Figure 2B:
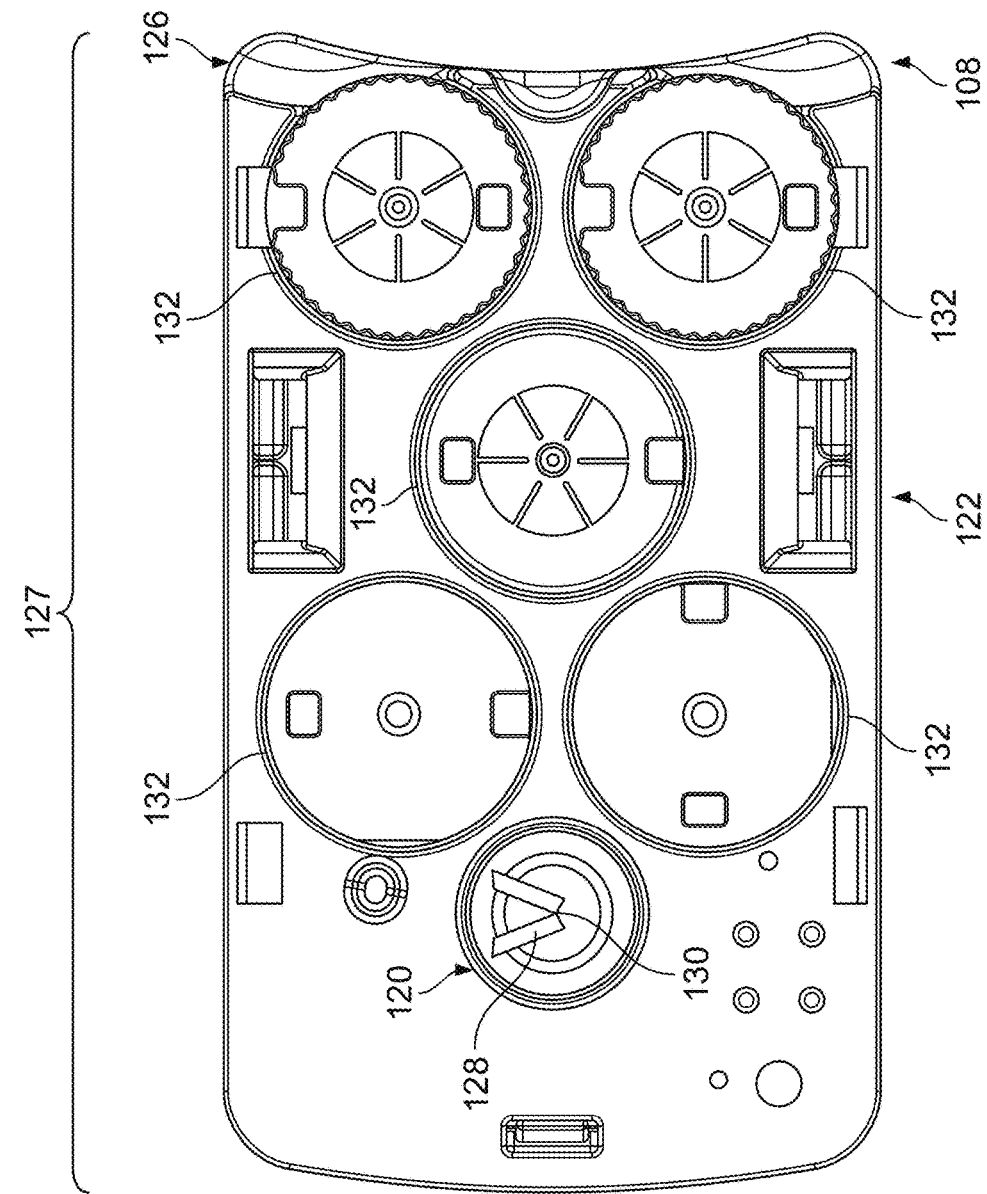
FIG. 2B is a bottom view of the drive assembly of FIG. 2A.
Figure 2A:
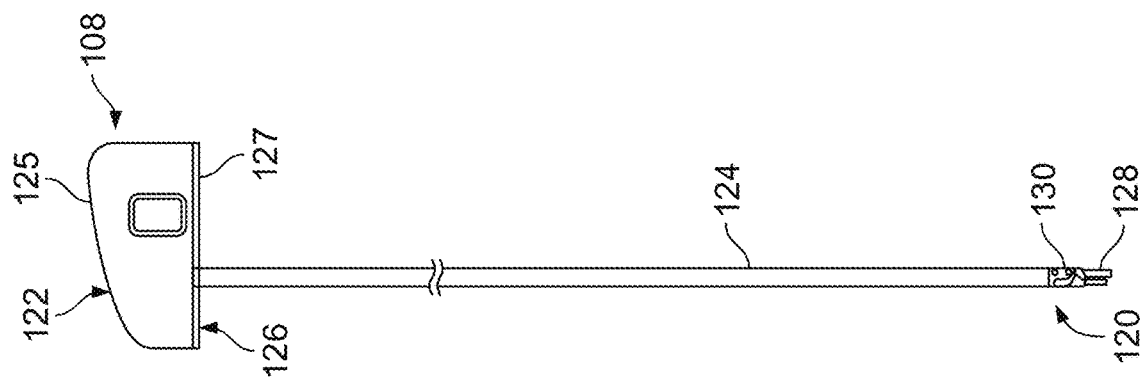
FIG. 2A is a side view of a surgical instrument including a drive assembly having an input device in accordance with one or more embodiments of the present disclosure.

FIG. 2A illustrates a surgical instrument 108 including a distal portion 120 and a proximal drive assembly 122 coupled to one another by an elongate shaft 124 defining an internal bore. Drive assembly 122 includes a housing 125 supporting an input device 126. Input device 126 includes an instrument control surface 127. The input device facilitates controlled adjustment of the instrument's end effector via a drive cable extending along the internal bore of the elongate instrument shaft.

Control surface 127 provides mechanical connections to the other control features of surgical instrument 108. During use, instrument control surface 127 couples to instrument carriage 106 (see FIG. 1), which controls surgical instrument 108, as generally described above. Distal portion 120 of surgical instrument 108 may provide any of a variety of surgical tools, such as the forceps 128 shown, a needle driver, a cautery device, a cutting tool, an imaging device (e.g., an endoscope or ultrasound probe), or a combined device that includes a combination of two or more various tools and imaging devices. Further, in the illustrated embodiment, forceps 128 are coupled to elongate shaft 124 by a wrist joint 130, which allows the orientation of the forceps to be manipulated with reference to the elongate shaft 124.

The bottom view of surgical instrument 108 shown in FIG. 2B illustrates control surface 127 of input device 126. As shown, control surface 127 includes a set of eight steering inputs 132, each of which governs a different aspect of movement by wrist joint 130 and forceps 128. Of course, more or less steering inputs 132 can be provided in different implementations. When control surface 127 is coupled to instrument carriage 106, each of steering inputs 132 interfaces with an actuator that drives the steering input. In this example, steering inputs 132 are configured to form a direct mechanical engagement with respective rotary actuators (e.g., servo motors) of instrument carriage 106. However, other suitable configurations for power transmission can also be used (e.g., indirect mechanical couplings including speed and/or torque converters, fluid couplings, and/or electrical couplings). Each of steering inputs 132 is part of a drive shaft (e.g., drive shaft 134 shown in FIGS. 3A-3B) that operates a drive cable (e.g., drive cable 166 shown in FIG. 5) controlling movement of forceps 128.

Figure 3A:
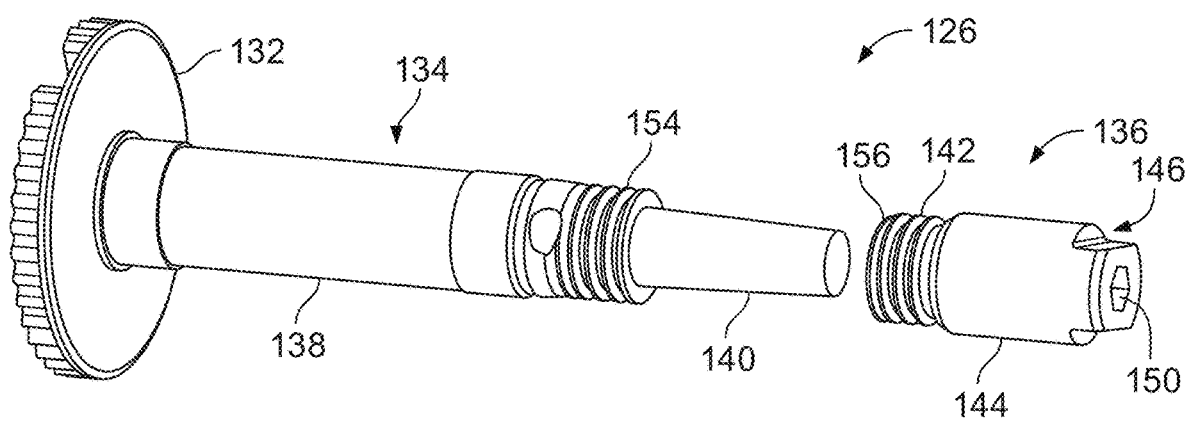
FIG. 3A is an exploded, perspective side view of a portion of a first input device including a drive shaft and a capstan.
Figure 3B:
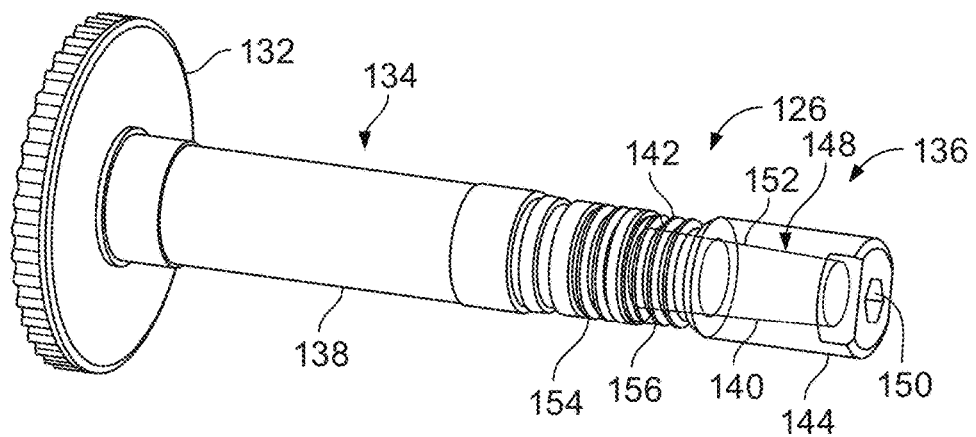
FIG. 3B is a perspective side view of the portion of the first input device with the capstan depicted transparently.

FIGS. 3A and 3B illustrate an isolated portion of input device 126. The illustrated portion of input device 126 includes a drive shaft 134 and a capstan 136. Drive shaft 134 and capstan 136 are separate and independent structures. These structures are depicted in FIG. 3B in an engaged state. As discussed in detail below, while in the engaged state, relative rotation between drive shaft 134 and capstan 136 is at least inhibited (or entirely prevented, in some examples). While in a disengaged state (see FIG. 5), the capstan 136 may be carried on the drive shaft 134, but relative rotation between them is freely permitted (i.e., uninhibited).

Drive shaft 134 includes the disk-shaped steering input 132 and a cylindrical rod 138 extending outward from the steering input along the steering input's axis of rotation. Drive shaft 134 further includes a support stem 140 extending from a central bore of cylindrical rod 138. In this example, steering input 132 and cylindrical rod 138 are thermoplastic parts (e.g., nylon or polycarbonate) that are overmolded around the metallic support stem 140.

Capstan 136 is a contiguous and monolithic tubular structure including a shank 142 and a head portion 144. Head portion 144 features a pair of opposing rectangular notches 146 that provide a structural coupling feature to facilitate engagement with an external device (e.g., drive mechanism 202 shown in FIG. 5) for rotating capstan 136 as part of a cable pre-tensioning process. As shown in FIG. 3B, capstan 136 includes a central through-bore 148 traversing both its shank 142 and head portion 144. Bore 148 includes an upper portion 150 and a lower portion 152. Drive shaft 134 and capstan 136 are simultaneously aligned and coupled to one another by inserting support stem 140 of drive shaft 134 into lower portion 152 of the capstan's central bore 148. When capstan 136 is disengaged from drive shaft 134 (yet still coupled (loosely) to the drive shaft), support stem 140 functions as a spindle that provides a central axis of rotation for the capstan. When capstan 136 is engaged with the drive shaft 134, mutual surface friction between the wall of bore 148 and support stem 140 provides a frictional force resisting relative rotation between the support stem and the capstan.

As noted above, input device 126 is specifically designed to carry a drive cable. During one exemplary use, one end of the drive cable is attached to drive shaft 134, and an opposite end of the drive cable is attached to capstan 136. In another exemplary use, one end of a first drive cable is attached to drive shaft 134, and one end of a second drive cable is attached to capstan 136. In some implementations, the drive cable end is crimped and coupled to the drive shaft 134 or capstan 136. In some implementations, purely frictional couplings may be used to attach the ends of the drive cable to drive shaft 134 and capstan 136. For example, the cable ends may be wound about these components for multiple revolutions to provide sufficient surface friction to maintain the couplings intact. As shown, both drive shaft 134 and capstan 136 include outwardly facing helical grooves 154, 156 to guide the winding of the cable ends. The middle portion of drive cable between the ends carried by input device 126 extends into the internal bore of the surgical instrument's elongate shaft 124. As described above, the drive cable traverses the internal bore and couples to an end effector or other distal end component of the surgical instrument. Power provided by an actuator of the instrument carriage is transmitted to drive shaft 134 via steering input 132, causing the drive shaft to rotate. With drive shaft 134 and capstan 136 in the engaged state, rotary motion imparted on the drive shaft is directly transferred to the capstan. Shared rotation of drive shaft 134 and capstan 136 may cause the respective ends of drive cable to equally release from or further entwine these components. More specifically, the cable ends may be wound about the drive shaft and capstan in opposite directions, such that their simultaneous rotation in a clockwise direction causes one end of the cable to release from the capstan while the other end becomes further wound about the drive shaft, and vice versa with counter-clockwise rotation. Such controlled movement of the drive cable facilitates operation of a "push/pull" or "pull/pull" mechanism for working the end effector.

Figure 4A:
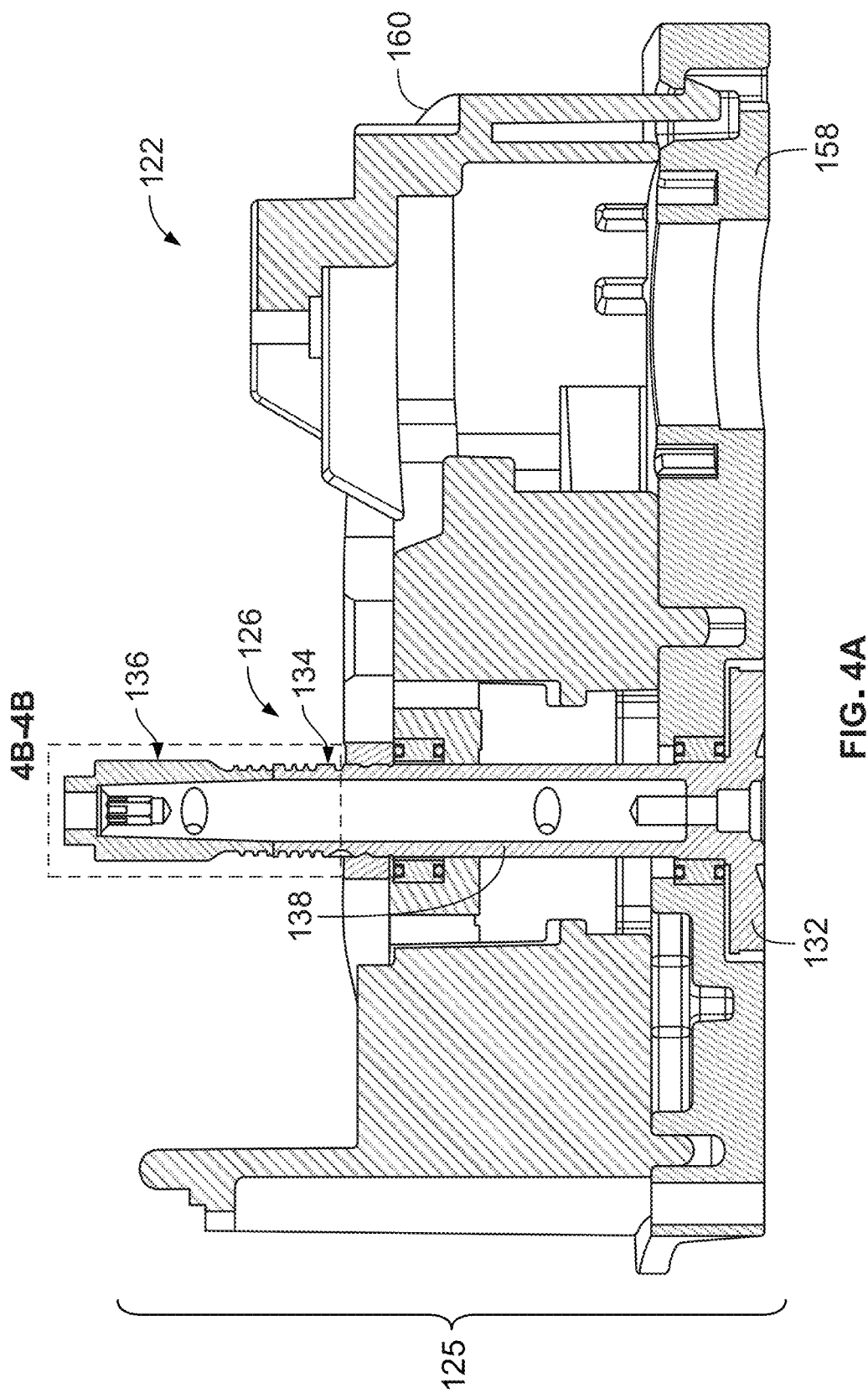
FIG. 4A is a cut-away side view of a portion of the drive assembly including the first input device of FIGS. 3A and 3B.

FIG. 4A depicts a portion of drive assembly 122, specifically housing 125, drive shaft 134, and capstan 136. In this example, housing 125 is a multi-component structure including a base 158 mounted to a carriage 160. Drive shaft 134 is rotatably mounted to housing 125, with steering input 132 supported within base 158 and cylindrical rod 138 supported in carriage 160. In addition to the structural features that accommodate the rod of drive shaft 134, carriage 160 also includes features for mounting other operative components of the drive assembly (e.g., spools, pulleys, etc.). Drive shaft 134 and capstan 136 are illustrated in FIG. 4A in an engaged state, such that the rotation of drive shaft 134 guided by the mounting hardware of housing 125 imparts identical motion to capstan 136. Engagement of drive shaft 134 and capstan 136 is facilitated by a taper friction fit between these components that at least inhibits, and in general prevents, relative rotation between them at the torques produced by cable tension.

Figure 4B:
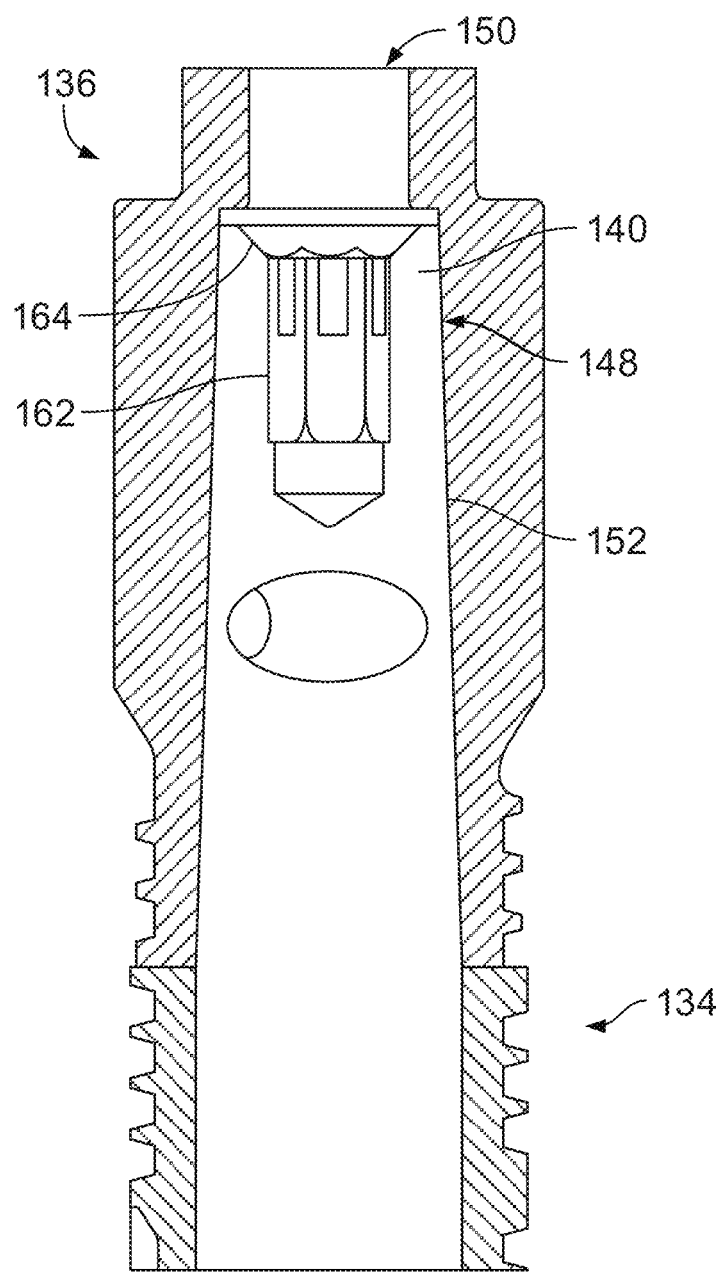
FIG. 4B is an enlarged view of the area in FIG. 4A marked 4B-4B.

Structural features enabling the formation of a taper friction fit are illustrated most clearly in FIG. 4B. As shown, lower portion 152 of the capstan's central bore 148 and support stem 140 of drive shaft 134 are mutually sized for surface-to-surface contact. In this example, the mating surfaces of support stem 140 and lower bore portion 152 are rounded and smooth, forming a frictional coupling that is both keyless and unthreaded. Thus, drive shaft 134 and capstan 136 can transition from the disengaged state to the engaged state by simply imparting a downward vertical force on capstan 136. As such, no additional alignment steps are necessary after the capstan is placed on the support stem of the drive shaft, which greatly simplifies the assembly and cable pre-tensioning processes. In this example, the mating surfaces of support stem 140 and lower bore portion 152 are not only rounded, but also radially tapered, defining support stem 140 and lower bore portion 152 as frustoconical shapes. The radial tapering aspect permits capstan 136 to sit loosely on the drive shaft's support stem 140 absent the external downward force (see FIG. 5). This permits the independent rotation of capstan 136 about the longitudinal axis of draft shaft 134 in the disengaged state.

Radial tapering of these components further enables the taper friction fit to function as a self-locking coupling. The term "self-locking," as used in the present disclosure, means that the mating surfaces of the capstan and drive shaft provides sufficient frictional force to prevent relative rotation between them under the forces/loads transmitted during a surgical procedure absent any external force. That is, with a self-locking coupling, the capstan is pressed down on the drive shaft to engage the two components and then removed, without disturbing the engagement. The self-locking coupling is maintained during use in a surgical procedure. A self-locking coupling is formed by providing the mating surfaces with a certain taper angle. This self-locking taper angle is a function of several variables, including material properties, surface roughness, expected rotational forces/loads, etc. In some particular implementations, we have found that the self-locking taper angle may be less than about 1.5 degrees (e.g., about 1.49 degrees).

As shown in FIG. 4B, the upper bore portion 150 of capstan 136 is coaxially aligned with a central blind bore 162 of support stem 140. These coaxial bores can be employed in conjunction with external hardware to facilitate engagement or disengagement of capstan 136 and drive shaft 134. For example, when the drive shaft-to-capstan taper friction fit forms a self-locking coupling, a lead screw may be used to release the capstan from the support stem. More specifically, in some implementations, upper bore portion 150 may include a pattern of internal threads designed to engage the threaded shank of a lead screw. Further, as shown, bore 162 includes a surface 164 (in this example a countersunk surface), which supports the lead screw and prevents further insertion of the screw into the bore. As shown, surface 162 forms a slight undercut with upper bore portion 150 to ensure contact between the lead screw and surface 162. Thus, removal of a self-locked capstan can be accomplished by inserting the lead screw into the threaded upper bore portion 150 and rotating the screw in the upper bore until the base of the screw presses against undercut surface 164 of support stem 140. Further rotation of the lead screw urges capstan 136 to ride up the threads of the lead screw, separating the capstan from the support stem 140. In some implementations, the capstan can be removed from the drive shaft by applying an upward external force to pull the two components apart.

The coaxial bores of drive shaft 134 and capstan 136 can also be used to maintain them in the engaged state—e.g., in the absence of a self-locking coupling. In this case, a mechanical fastener, such as a threaded set screw, can be used to lock the capstan to the drive shaft. More specifically, in some implementations, the blind bore 162 of support stem 140 may also be threaded and designed to interface with the threaded shank of the set screw. When the set screw is tightened, it bears down against the capstan and provides a constant downward force to augment and maintain the surface friction force of the coupling.

In one implementation of the coupling between drive shaft 134 and capstan 136, the capstan is placed over the drive shaft so that it can rotate. One cable end is secured to and wrapped around the drive shaft, and another cable end is secured to and wrapped around the capstan. The drive shaft is rotated until its corresponding cable is at a desired tension, and then the drive shaft is held in position to maintain the tension. Next, the capstan is rotated until its corresponding cable is at a desired tension, and then the capstan is held in position to maintain the tension. Optionally, the drive shaft and capstan are simultaneously rotated to establish the cable tensions. When both cables are at the desired tension, a force (e.g., a hammer strike) is applied to drive the capstan against the drive shaft and create an engaged first friction coupling between the capstan and drive shaft. The first friction coupling temporarily prevents relative rotation between drive shaft and capstan, even though their corresponding cables urge the rotation. While the first friction coupling holds the capstan in place, an axially-aligned set screw or other suitable fastener is applied to further urge the capstan downward against the drive shaft to augment the first friction coupling and maintain a larger engaged second friction coupling, and so maintain the desired tension in the cables.

Figure 5:
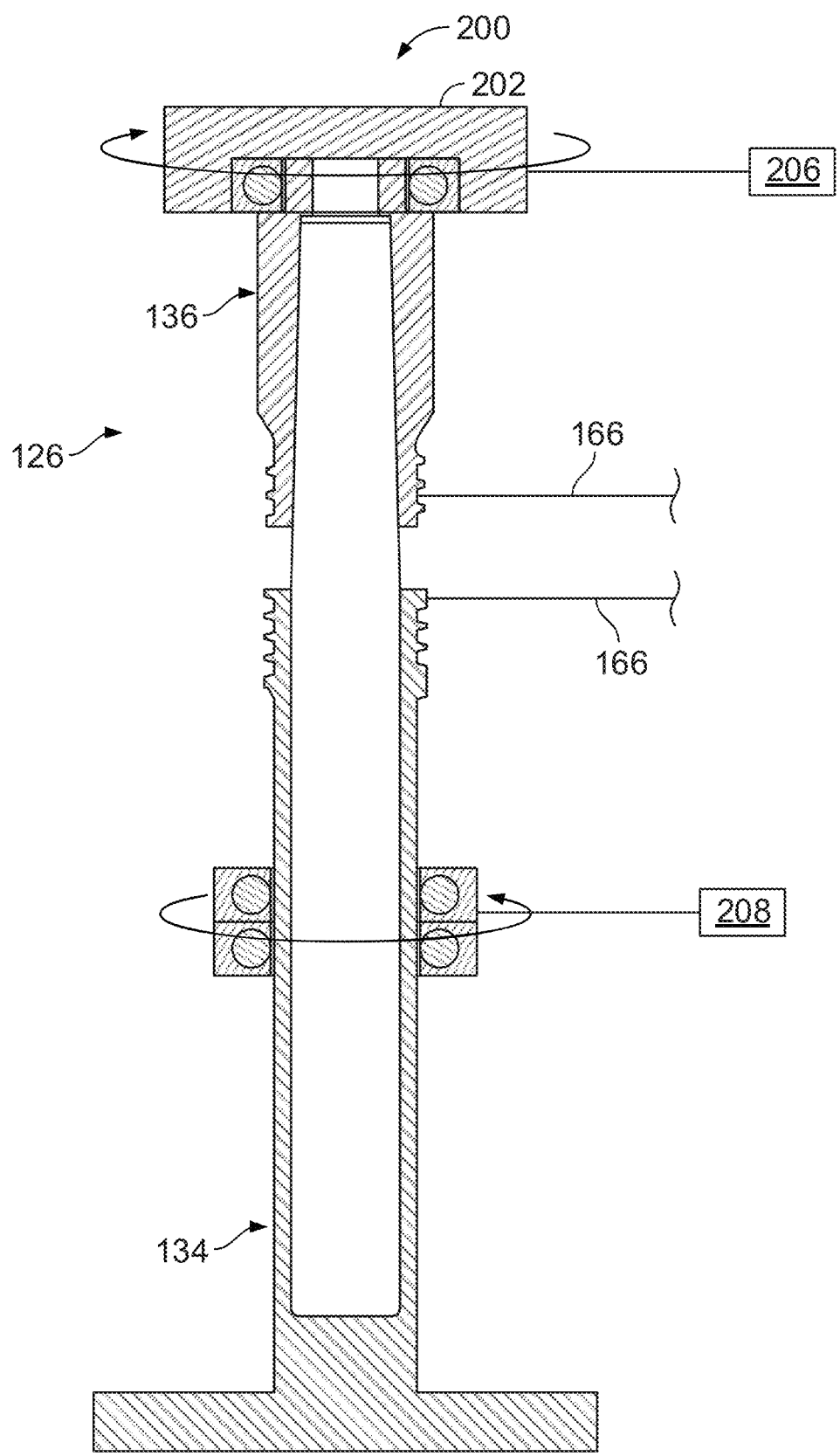
FIG. 5 is a functional diagram of the first input device illustrating a method for tensioning a drive cable of the assembly.

Referring next to FIG. 5, pre-tensioning of a drive cable 166 can be performed using an apparatus 200 appropriately configured to independently rotate drive shaft 134 and capstan 136 when these components in the disengaged state. In this example, apparatus 200 includes a first drive mechanism 202 and a second drive mechanism 204. First drive mechanism 202 is powered by a first motor 206, and second drive mechanism 204 is powered by a second motor 208. As shown, drive shaft 134 is carried by first drive mechanism 202, and capstan 136 is carried by second drive mechanism 204. As discussed below, the two drive mechanisms can be used to pre-tension the drive cable by rotating the drive shaft and capstan alternatively (i.e., one at a time) or simultaneously.

Figure 6:
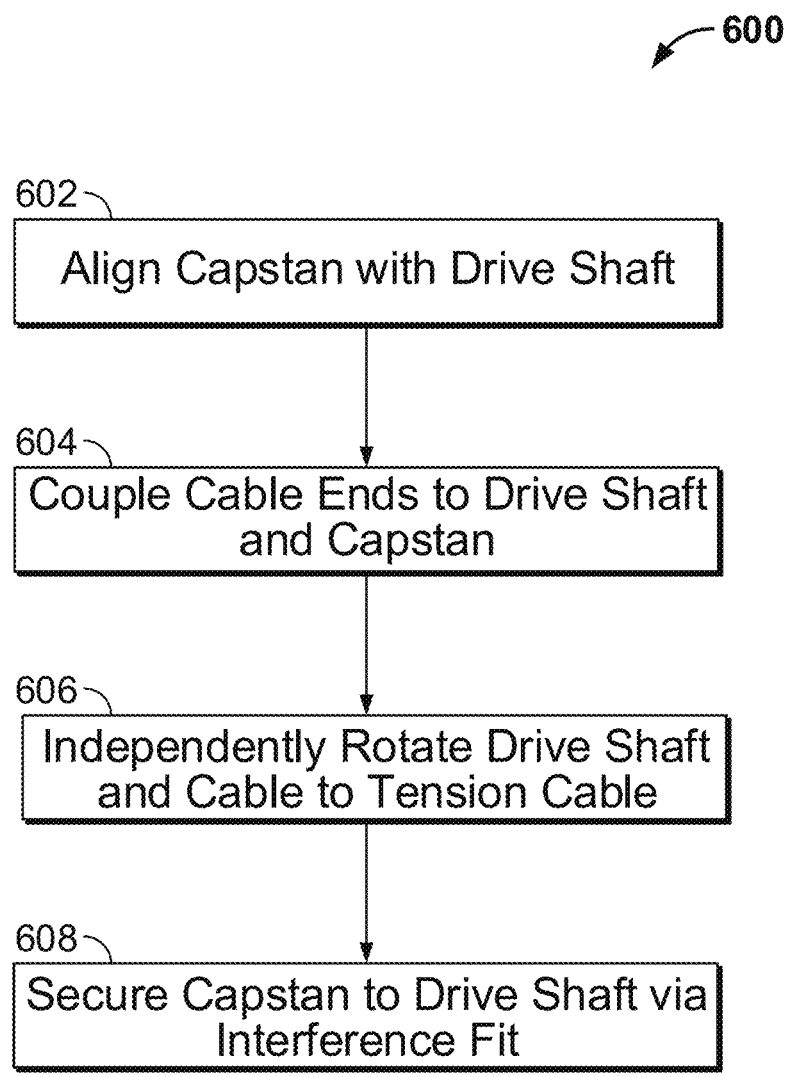
FIG. 6 is a flow chart illustrating a first method of tensioning a cable of a drive assembly for a surgical instrument.

FIG. 6 illustrates a method 600 of tensioning a cable of a drive assembly for a surgical instrument. For purposes of clarity, the method 600 will be described in the context of apparatus 200 and input device 126, the individual components of which are described above. Step 602 of method 600 includes aligning capstan 136 with drive shaft 134 in a disengaged state. For example, the capstan may be placed over and on top of the drive shaft absent external force. In particular, the support stem of the drive shaft can be inserted into the lower portion of a central through-bore traversing the capstan. When radially tapered surfaces are used, the capstan sits loosely on the support stem, coupling the capstan to the drive shaft in a disengaged state.

Step 604 includes coupling the respective ends of drive cable(s) 166 to drive shaft 134 and capstan 136. In some examples, the ends of the cable(s) are attached to the drive shaft and capstan by purely frictional couplings, absent additional connection hardware (e.g., crimps or other fasteners). For instance, the cable ends may be wound around the drive shaft and capstan. Step 606 includes independently rotating drive shaft 134 and capstan 136 to draw drive cable(s) 166 into tension. As discussed above, such independent rotation can be performed when the capstan is placed over the drive shaft, rotationally supported by the shaft's support stem, and the components are in the disengaged state. Independent rotation of the drive shaft 134 and capstan 136 may be performed by separately powering first and second drive mechanisms 202, 204 via first and second motors 206, 208. In some examples, the drive shaft and capstan can be rotated alternatively, with one of the components being held fixed while the other is driven. In some other examples, the drive shaft and capstan can be rotated simultaneously.

Step 608 includes securing capstan 136 to drive shaft 134 in an engaged state. Securing the capstan may include applying a downward vertical force against the capstan to drive it down against the stem portion of the drive shaft. The downward vertical force causes the radially tapered surface of the capstan's lower bore portion to bear against the radially tapered outer surface of the drive shaft's support stem. The mutual force exerted by these mating surfaces against one another provides sufficient friction to inhibit relative movement between the drive shaft and capstan. In some examples, the radial taper of the surfaces defines a self-locking taper, allowing the capstan and drive shaft to remain engaged absent the downward force. In some other examples, a set screw may be inserted through coaxially aligned bores of the capstan and support stem to maintain the downward force that facilitates the taper friction fit coupling.

In some implementations, the capstan may be released from the support stem of the drive shaft to allow for further tensioning of the drive cable. If the taper friction fit between the capstan and drive shaft is not self-locking, the capstan can be released by removing the set screw. Release of a self-locking capstan may involve the use of a lead screw. For example, the lead screw may be inserted into a threaded bore of the capstan and rotated until it bears against a surface of the support stem to urge the capstan apart from the stem. As such, further tensioning can be performed by releasing the capstan, again independently rotating the capstan and drive shaft, and then re-engaging the capstan and the drive shaft.

Figure 7A:
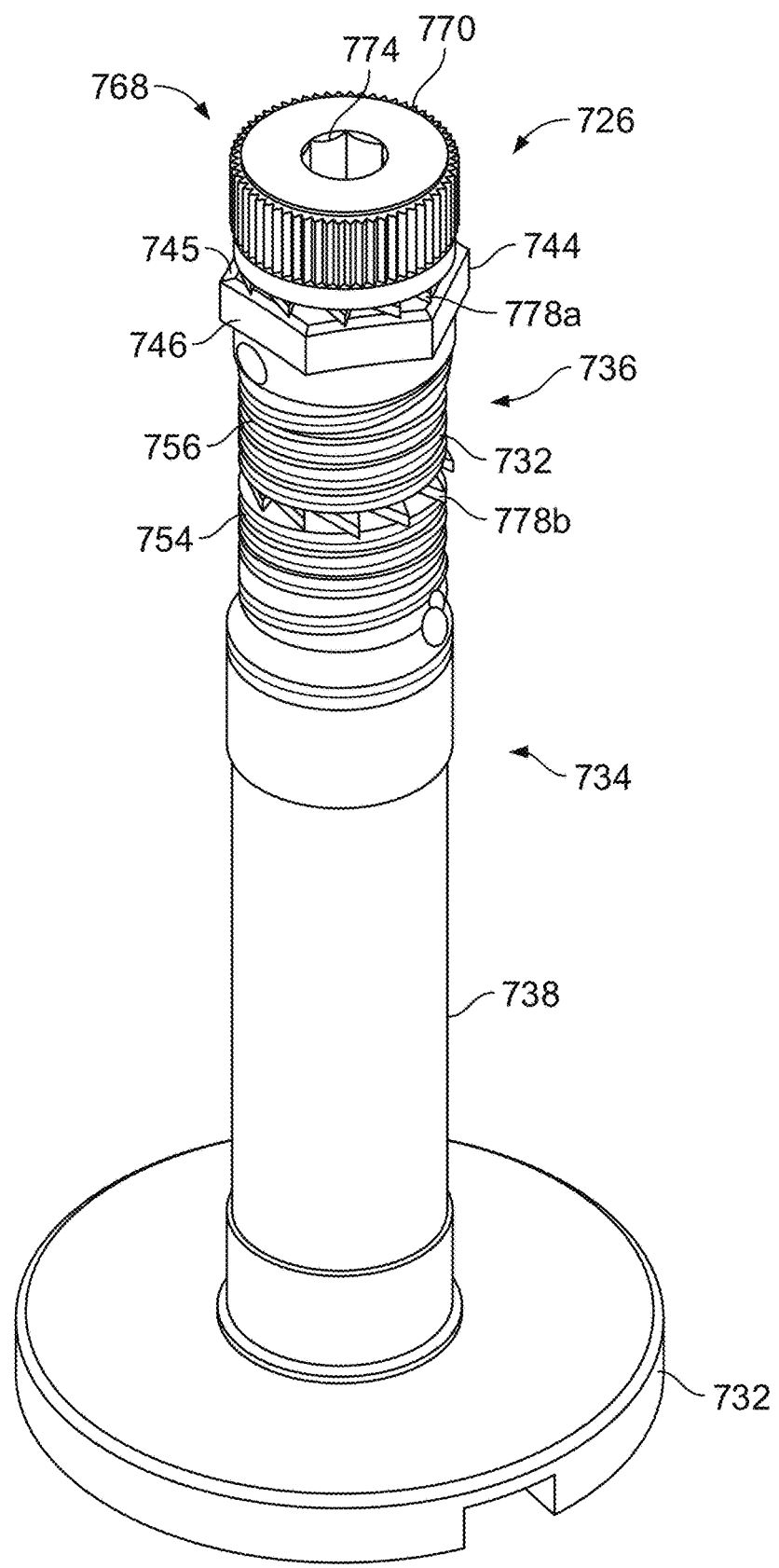
FIGS. 7A and 7B are perspective and cut-away side views of a second input device including a drive shaft and a capstan.
Figure 7B:
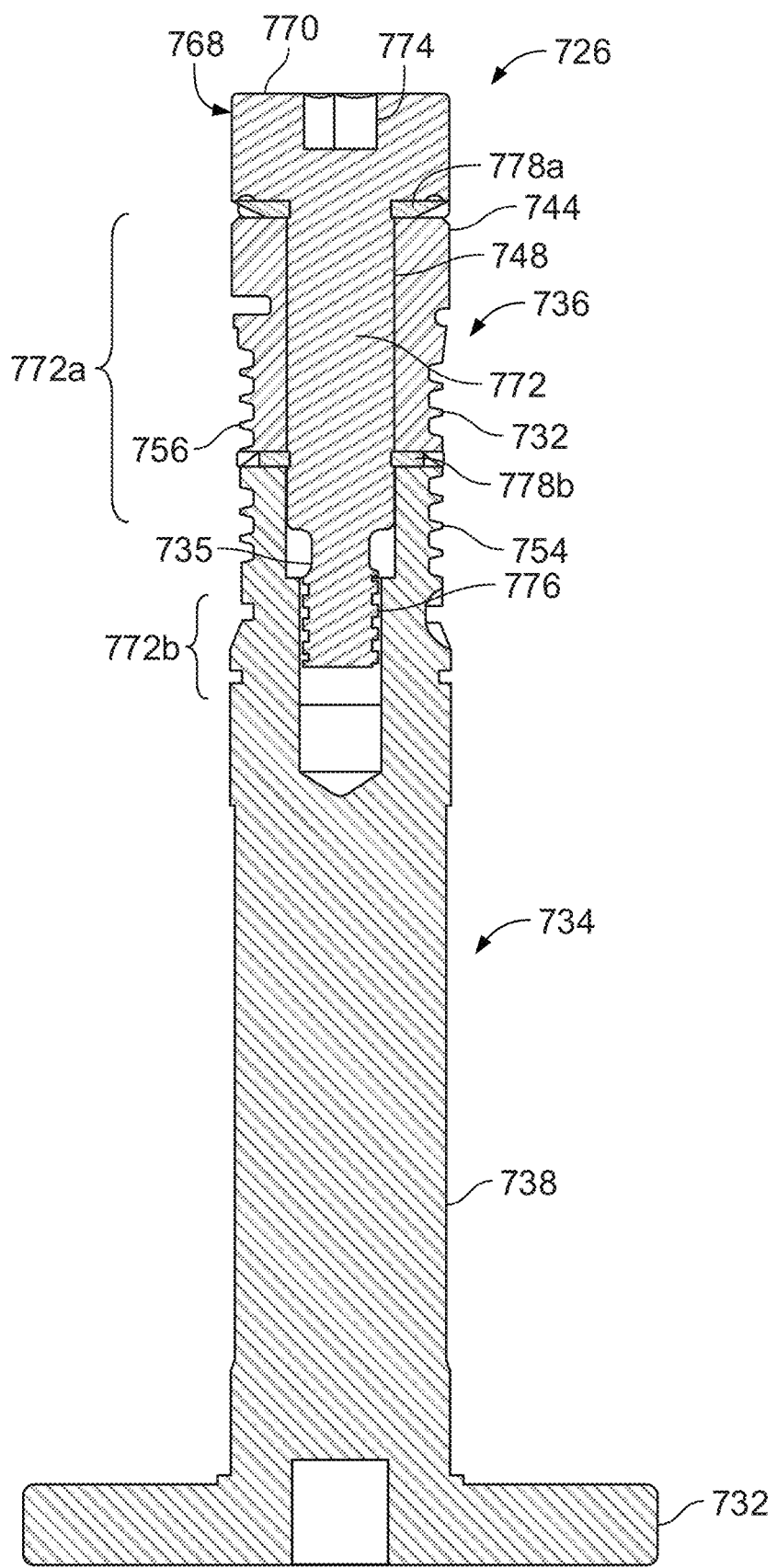

FIGS. 7A and 7B illustrate an isolated portion of a second exemplary input device 726. Similar to input device 126 of FIGS. 3A and 3B, input device 726 includes a drive shaft 734 and a capstan 736 that are separate and independent structures capable of being reversibly adjusted between an "engaged state" (as shown) and a "disengaged state" for pre-tensioning and securing one or more drive cables. Drive shaft 734 includes a disk-shaped input 732 and a cylindrical rod 738 extending outward from the input. In this example, drive shaft 734 further includes a central blind bore 735 (see FIG. 7B) having interior screw threads for receiving and engaging a set screw 768. Drive shaft 734 still further includes exterior, outwardly facing helical grooves 754 to guide the winding of cable ends for forming a frictional coupling to the drive shaft. Alternatively, cable ends may be secured to the drive shaft and capstan as described above.

Capstan 736 includes a shank 742 and a head portion 744. As shown, head portion 744 has a polygonal cross-section (hexagonal, in this example) with planar top and side surfaces 745, 746. Planar top surface 745 engages a first toothed washer 778a. Planar side surfaces 746 are configured to engage the bore of a socket-type tensioning tool 880, as described below with reference to FIG. 8. Shank 742 is generally cylindrical in shape, and, like drive shaft 734, includes a set of exterior, outwardly facing helical grooves 756 to guide the winding of cable ends. Shank 742 also includes a planar bottom surface 747 that engages a second toothed washer 778b. Further still, as shown in FIG. 7B, capstan 736 includes a central through-bore 748 of constant diameter that axially traverses both shank 742 and head portion 744.

As noted above, input device 726 includes a set screw 768. Set screw 768 is designed to couple capstan 736 to drive shaft 734, and to facilitate adjustment between the engaged and disengaged state of these components. Set screw 768 includes a radially enlarged head 770 centered atop a generally cylindrical shaft 772. Head 770 features a keyed blind bore 774 (e.g., a hex keyed bore) and a planar bottom surface for engaging the first toothed washer 778a.

Shaft 772 includes an upper portion 772a and a lower portion 772b. The upper portion of the shaft has an enlarged diameter relative to the lower portion. In particular, the diameter of upper portion 772a closely matches the diameter of the capstan's through-bore 748, which enables shaft 772 to function as a spindle that provides a central axis of rotation for capstan 736 in the disengaged state. Lower portion 772b includes a set of exterior screw threads 776 that engage the interior threads of the drive shaft's blind bore 735. Engagement of these mating screw threads secures set screw 768 to drive shaft 734, and therefore also couples capstan 736 to the drive shaft. That is, the capstan is retained between the drive shaft and the head of the set screw. The initial engagement of the threads places the device in the disengaged state, leaving capstan 736 free to rotate about the upper portion (772a) of set screw shaft 772. Further rotation of set screw 768 progressively advances shaft 772 downward along the threaded blind bore 735 of drive shaft 734 until capstan 736 becomes effectively clamped between the head of the set screw and the drive shaft. This places the device in the engaged state.

In this example, input device 726 features an assembly of machined metal parts designed for withstanding relatively high torque loads during use of the surgical instrument. The advantage of utilizing metal-to-metal interfaces between clamping elements is increased slip resistance. Slippage between the capstan and drive shaft significantly degrades the degree of precision in controlling the surgical instrument's end effector because it introduces slack or less than desired tension in the drive cable(s). In a particular implementation, set screw 768 is composed of alloy steel, drive shaft 734 and capstan 736 are composed of aluminum (e.g., 6061-T651 aluminum), and toothed washers 779a,b are composed of stainless steel (e.g., 316 stainless steel). In these implementations, the hardness of the washers is greater than the hardness of the capstan, which allows the teeth of the washers to "bite" into the capstan to increase the hold between these components. This configuration exhibited an acceptable "slip limit" (i.e., the amount of torque applied at the onset of slippage) ranging between 80 and 160 ounce-inch of torque.

Figure 8:
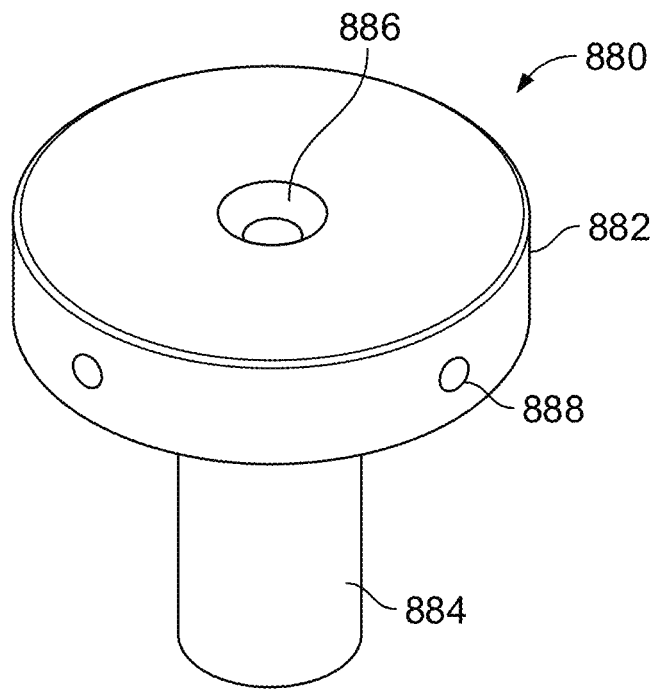
FIG. 8 is a perspective view of a tensioning tool for use in conjunction with the second input device.
Figure 9:
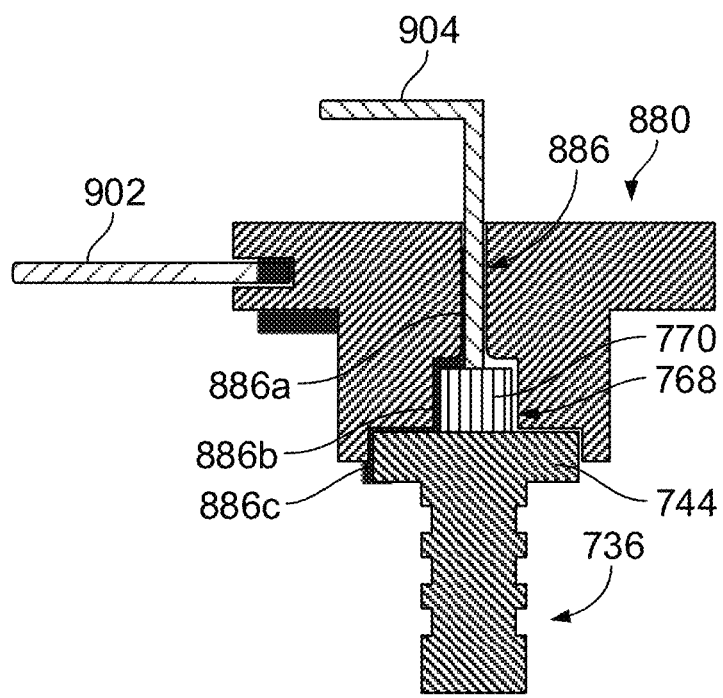
FIG. 9 is a cut-away diagram illustrating use of the tensioning tool of FIG. 8 to tension a drive cable carried by the second input device of FIGS. 7A and 7B.

FIGS. 8 and 9 depict a tool 880 for facilitating the pre-tensioning of one or more drive cables carried by input device 726. Tensioning tool 880 includes an enlarged flathead 882 and a shank 884. A central through-bore 886 axially traverses both flathead 882 and shank 884. As shown in FIG. 9, bore 886 includes a first portion 886a, a second portion 886b, and a third portion 886c of discretely increasing diameters. The first bore portion 886a is appropriately sized to receive a hex-profiled wrench 904 (i.e., an Allen wrench) that engages the hex-keyed blind bore 774 of set screw 768. The second bore portion 886b is appropriately sized to receive the head 770 of set screw 768. The third bore portion 886c is appropriately sized to receive the head portion 744 of capstan 736. This third portion 886c further includes a polygonal profile that engages the planar side surfaces of 746 of the head portion 744.

To perform the cable pre-tensioning procedure, the device is placed in the disengaged state by loosely coupling capstan 736 to drive shaft 734 via set screw 768 (e.g., by initially engaging the set screw threads with the drive shaft threads, but not tightening down the set screw). The tensioning tool 880 is then fitted over the capstan 736, and a tensioning wand 902 inserted into a sidewall aperture 888 of flathead 882 is used to rotate the capstan relative to drive shaft 734 (e.g., by exerting a force on the wand that is tangential to the capstan). When a predetermined degree of pre-tensioning has been reached, the position of flathead 882 is held fixed as the profiled wrench 904 is inserted into the central bore 886 of tensioning tool 880 and used to tighten set screw 768 via the blind bore 774.

Figure 10:
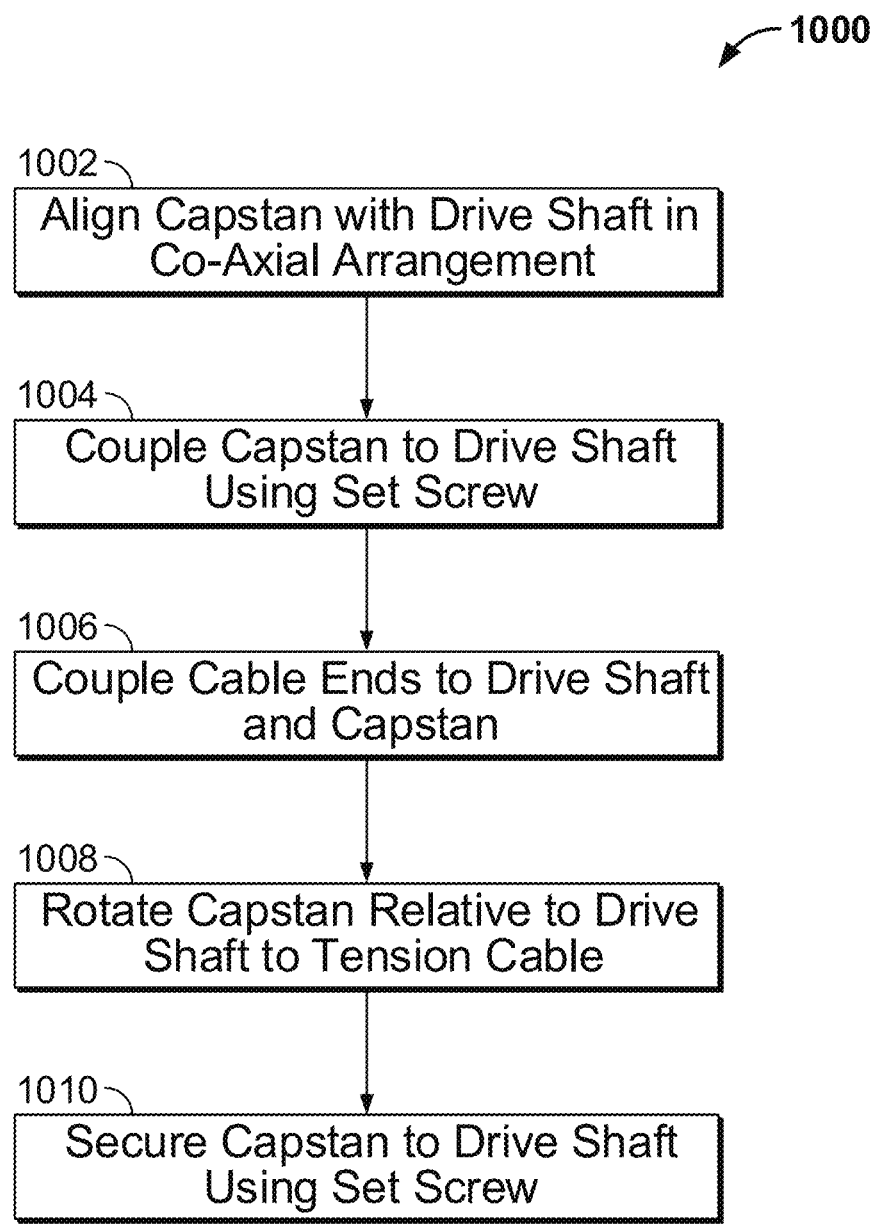
FIG. 10 is a flow chart illustrating a second method of tensioning a cable of a drive assembly for a surgical instrument.

FIG. 10 illustrates a method 1000 of tensioning a cable of a drive assembly for a surgical instrument. For purposes of clarity, the method 1000 will be described in the context of tensioning tool 880 and input device 726, the individual components of which are described above. Step 1002 of method 1000 includes aligning capstan 736 with drive shaft 734. This alignment step places the central through-bore 748 of the capstan in a co-axial arrangement with the blind bore 735 of the drive shaft absent significant external forces. Step 1004 includes coupling the capstan 736 to the drive shaft 734 in a disengaged state. While in the disengaged state, the capstan and drive shaft are freely rotatable relative to one another. Coupling the capstan to the drive shaft in the disengaged state may include inserting the shaft of set screw 768 through the co-axially aligned through-bore of the capstan and blind bore of the drive shaft. Further, in some examples, a set of exterior screw threads on the shaft of the set screw can be engaged with a set of interior screw threads of the blind bore of the drive shaft. This initial threaded engagement retains the capstan between the drive shaft and the head of the set screw, but does not exert a clamping force to lock the capstan in place. Step 1006 includes coupling the respective ends of a drive cable to drive shaft 734 and capstan 736. As discussed above in connection with the method 600, in some examples, the ends of the cable are attached to the drive shaft and capstan by purely frictional couplings, absent additional connection hardware (e.g., crimps or other fasteners). For instance, the cable ends may be wound around the drive shaft and capstan.

Step 1008 includes rotating capstan 736 relative to drive shaft 734 to tension the drive cable(s). And, step 1010 includes securing the capstan 736 to the drive shaft 734 in an engaged state. In some examples, tensioning tool 880 can be used to facilitate the rotating (step 1008) and securing (step 1010) of capstan 736. For example, the tensioning tool can be placed over the capstan, such that the bore of the tool is keyed to the head of the capstan. Then, tensioning wand 902 can be engaged with tensioning tool 880 to rotate the tool and the keyed capstan relative to the drive shaft. When the desired cable tension is reached, the tensioning wand 902, and therefore flathead 882, is held in place to inhibit (or prevent) further rotation of the capstan while wrench 904 is inserted through the central bore of tensioning tool 880 to tighten set screw 768. Tightening the set screw advances the shaft of the screw through the blind bore of the drive shaft along the engaged threads until the head of the screw clamps down on the capstan with sufficient force to lock it in place.

The use of terminology such as "top," "bottom," "over," "downward," "upper," "lower," etc. throughout the specification and claims is for describing the relative positions of various components of the system and other elements described herein. Similarly, the use of any horizontal or vertical terms to describe elements is for describing relative orientations of the various components of the system and other elements described herein. Unless otherwise stated explicitly, the use of such terminology does not imply a particular position or orientation of the system or any other components relative to the direction of the Earth gravitational force, or the Earth ground surface, or other particular position or orientation that the system other elements may be placed in during operation, manufacturing, and transportation.

A number of embodiments of the invention have been described. Nevertheless, it will be understood that various modifications may be made without departing from the spirit and scope of the inventions. In addition, it should be understood that various described components and features optionally may be combined, so that one or more features of one embodiment may be combined with, or substituted for, one or more features of another embodiment consistent with the inventive aspects.

What is claimed is:

1. A surgical instrument, comprising:
an adjustable end effector;
an elongated instrument shaft defining an internal bore and extending from a first end coupled to the end effector to a second end; and
a drive assembly comprising a housing coupled to the second end of the instrument shaft and an input device configured to facilitate controlled adjustment of the end effector via a drive cable extending along the bore of the instrument shaft, the input device comprising:
a drive shaft attached to a first portion of the drive cable, the drive shaft comprising an upstanding stem portion having a radially tapered outer surface; and
a capstan attached to a second portion of the drive cable, the capstan defining an internal bore sized to receive the stem portion of the drive shaft, at least a lower portion of the internal bore having a radially tapered inner surface,
wherein the capstan and drive shaft are configured to transition from a disengaged state, where the capstan is freely rotatable about a longitudinal axis of the drive shaft, to an engaged state, where surface friction between the radially tapered surfaces of the drive shaft and capstan inhibits relative rotation as the end effector is adjusted during a surgical procedure,
wherein the radial taper of the radially tapered surfaces defines a self-locking taper angle, such that the capstan and drive shaft remain in the engaged state absent an external force, and
wherein the self-locking taper angle is less than about 1.5 degrees.

2. The surgical instrument of claim 1, wherein the outer surface of the stem portion of the drive shaft and the inner surface of the lower portion of the internal bore of the capstan are rounded, forming a keyless and unthreaded frictional coupling in the engaged state.

3. The surgical instrument of claim 1, wherein a head portion of the capstan comprises a structural coupling feature configured to facilitate engagement with an external device for rotating the capstan in the disengaged state.

4. The surgical instrument of claim 1, wherein an upper portion of the internal bore of the capstan is coaxially aligned with a blind bore of the stem portion of the drive shaft, and wherein the upper portion of the internal bore comprises a pattern of threads for interfacing with a threaded lead screw, and wherein the blind bore of the stem portion comprises and undercut surface for supporting the lead screw.

5. The surgical instrument of claim 4, wherein the blind bore of the stem portion includes a pattern of threads for interfacing with a threaded mechanical fastener projecting through the coaxially aligned bores of the drive shaft and capstan, the mechanical fastener applying a constant axial force against the drive shaft and capstan to augment the surface friction.

6. A method of tensioning a cable of a drive assembly for a surgical instrument having an adjustable end effector, the method comprising:
aligning a capstan with a drive shaft of the drive assembly in a disengaged state, the drive shaft comprising an upstanding stem portion having a radially tapered outer surface, and the capstan comprising an internal bore having a radially tapered inner surface, with at least a lower portion of the bore receiving the stem portion;
coupling respective portions of the cable to the drive shaft and to the capstan; and then
independently rotating the drive shaft and the capstan about a common longitudinal axis to tension the cable; and
after tensioning the cable, securing the capstan to the drive shaft in an engaged state by forcing the radially tapered inner surface of the internal bore of the capstan against the radially tapered outer surface of the stem portion of the drive shaft, such that surface friction between the radially tapered surfaces inhibits relative rotation between the drive shaft and capstan as the end effector is adjusted during a surgical procedure, wherein the radial taper of the radially tapered surfaces defines a self-locking taper angle, such that the capstan and drive shaft remain in the engaged state absent an external force, and wherein the self-locking taper angle is less than about 1.5 degrees.

7. The method of claim 6, wherein rotating the capstan comprises driving the capstan rotationally about the stem portion of the drive shaft, and wherein independently rotating the drive shaft and the capstan comprises simultaneously rotating the drive shaft and capstan in opposite angular directions.

8. The method of claim 6, wherein aligning the capstan with the drive shaft comprises placing the capstan over the drive shaft absent external force, and wherein securing the capstan to the drive shaft in an engaged state comprises applying a vertical force against the capstan to drive the capstan down against the stem portion of the drive shaft.

9. The method claim 6, the method further comprising:
releasing the capstan from the drive shaft to transition from the engaged state to the disengaged state;
further tensioning the cable to a predetermined set point by independently rotating the drive shaft and the capstan; and
after further tensioning the cable, re-securing the capstan to the drive shaft to transition from the disengaged state to the engaged state.

10. The method of claim 9, wherein releasing the capstan from the drive shaft comprises:
inserting a lead screw into the internal bore of the capstan, and
urging the capstan to move along a threaded shaft of the lead screw, as the lead screw bears against a surface of the drive shaft.

11. The method claim 6, wherein securing the capstan to the drive shaft further includes inserting a set screw into an upper portion of the internal bore of the capstan and a blind bore of the stem portion of the drive shaft, the blind bore being coaxially aligned with the internal bore.

12. A surgical instrument, comprising:
an adjustable end effector;
an elongated instrument shaft defining an internal bore and extending from a first end coupled to the end effector to a second end; and
a drive assembly comprising a housing coupled to the second end of the instrument shaft and an input device configured to facilitate controlled adjustment of the end effector via a drive cable extending along the bore of the instrument shaft, the input device comprising:

a drive shaft attached to a first portion of the drive cable, the drive shaft comprising a central blind bore and an upstanding stem portion having a radially tapered outer surface;

a capstan attached to a second portion of the drive cable, the capstan defining a central through-bore co-axially alignable with the blind bore of the drive shaft, and the capstan comprising a radially tapered inner surface sized to receive the stem portion of the drive shaft, and a set screw comprising a radially enlarged head centered atop an elongated shaft, the shaft comprising an upper portion sized to penetrate the through-bore of the capstan and a lower portion sized to penetrate the blind bore of the drive shaft, wherein the capstan and drive shaft are configured to transition from a disengaged state, where the capstan is freely rotatable about the upper portion of the shaft of the set screw, to an engaged state, where a compressive clamping force between the set screw and drive shaft locks the capstan in place to inhibit relative rotation as the end effector is adjusted during a surgical procedure.

13. The surgical instrument of claim 12, wherein the upper portion of the shaft of the set screw has a larger diameter than the lower portion of the shaft.

14. The surgical instrument of claim 12, wherein an inner surface of the through-bore of the capstan and an outer surface of the upper portion of the shaft of the set screw are rounded, forming a keyless and unthreaded engagement.

15. The surgical instrument of claim 12, wherein the head of the set screw comprises a blind bore having a keyed profile for engaging a wrench device.

16. The surgical instrument of claim 12, wherein the lower portion of the shaft of the set screw comprises a set of exterior threads configured to mate with a complementary set of interior threads of the blind bore of the drive shaft.

17. The surgical instrument of claim 12, further comprising a first toothed washer residing axially between the head of the set screw and the capstan, and a second toothed washer residing axially between the capstan and the drive shaft, and wherein the hardness of the material composition of each of the toothed washers is greater than the hardness of the material composition of the capstan.

* * * * *